United States Patent
Reichel

(10) Patent No.: US 8,494,112 B2
(45) Date of Patent: Jul. 23, 2013

(54) SYSTEM AND METHOD FOR TRANSFERRING DATA IN A COMPUTED TOMOGRAPHY APPARATUS

(75) Inventor: Werner Reichel, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 239 days.

(21) Appl. No.: 13/006,923

(22) Filed: Jan. 14, 2011

(65) Prior Publication Data

US 2011/0176654 A1    Jul. 21, 2011

(30) Foreign Application Priority Data

Jan. 21, 2010   (DE) .......................... 10 2010 005 284

(51) Int. Cl.
*H05G 1/60*    (2006.01)
(52) U.S. Cl.
USPC ................................. 378/15; 378/4
(58) Field of Classification Search
USPC .......................... 378/4, 15, 91, 210
See application file for complete search history.

(56) References Cited

U.S. PATENT DOCUMENTS

| | | | |
|---|---|---|---|
| 4,697,092 | A | 9/1987 | Roggendorf et al. |
| 4,926,158 | A | 5/1990 | Zeigler |
| 5,208,581 | A | 5/1993 | Collins |
| 6,798,309 | B2 | 9/2004 | Lohr et al. |
| 7,421,058 | B2 | 9/2008 | Popescu et al. |
| 7,717,619 | B2 * | 5/2010 | Katcha et al. ................. 378/197 |
| 2002/0193075 | A1 | 12/2002 | Lohr |

OTHER PUBLICATIONS

"One-Wire Smart Motors Communicating over the DC Power Bus-Line with Application to Endless Rotary Joints," Wade et al., Proceedings of the 2002 IEEE International Conference on Robotics and Automation (2002) pp. 2369-2374.
"System Integration of the MiCES Small Animal PET Scanner," Lewellen et al., IEEE Nuclear Science Symposium Conference Record, vol. 5 (2004) pp. 3316-3320.
"Powerline Communications: Finally Ready for Prime Time?" Clark, IEEE Internet Computing, vol. 2, No. 1 (1998) pp. 10-11.

* cited by examiner

*Primary Examiner* — Jurie Yun
(74) *Attorney, Agent, or Firm* — Schiff Hardin LLP

(57) ABSTRACT

In a method and system for data transfer in a computed tomography apparatus having a gantry with a rotatable part and a stationary part, at least one device is provided for energy transfer between the rotatable part and stationary part of the gantry and at least one PLC (Power Line Communication) component is provided for data transfer between the rotatable part and the stationary part of the gantry via at least one device for energy transfer.

13 Claims, 2 Drawing Sheets

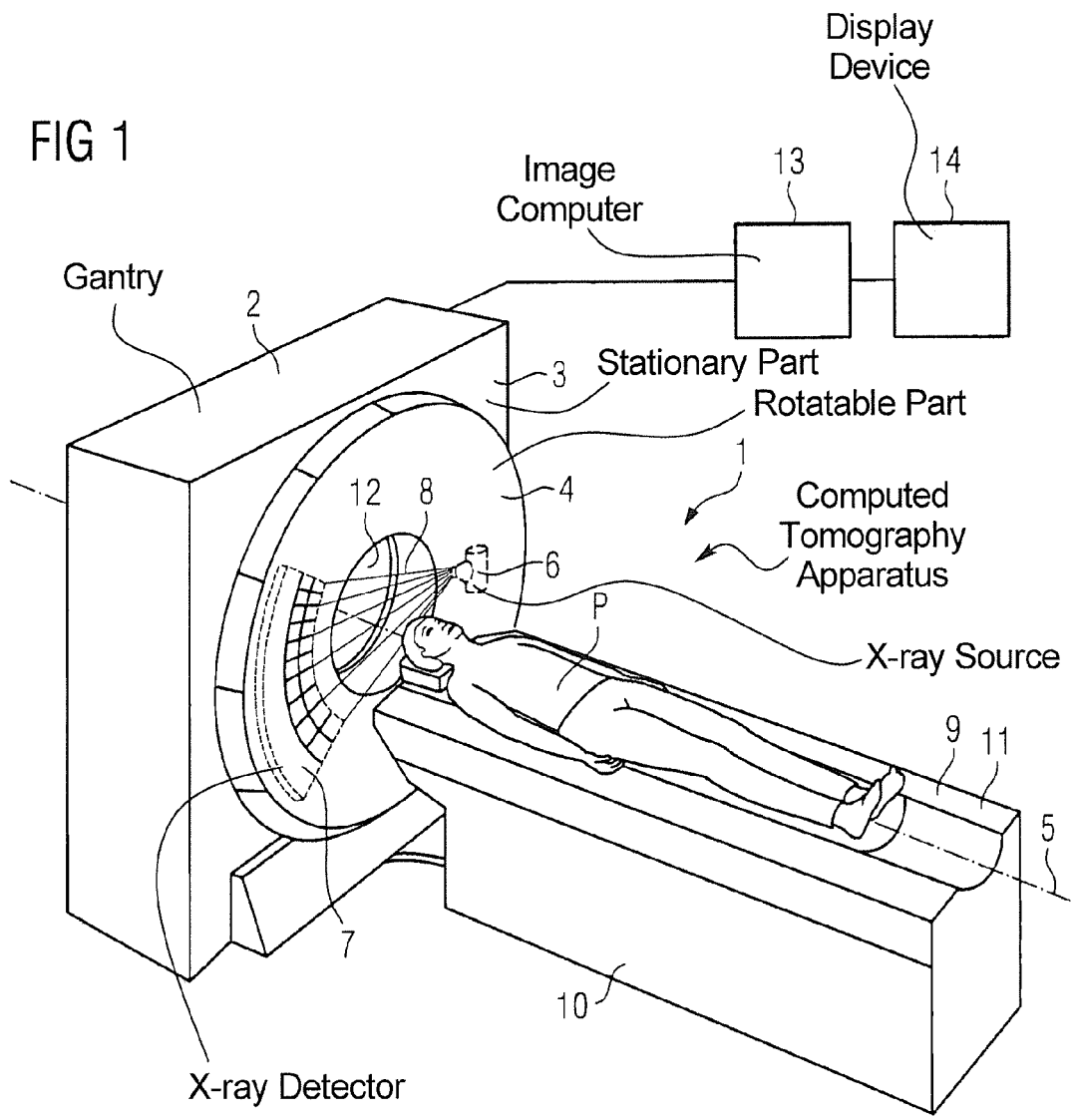

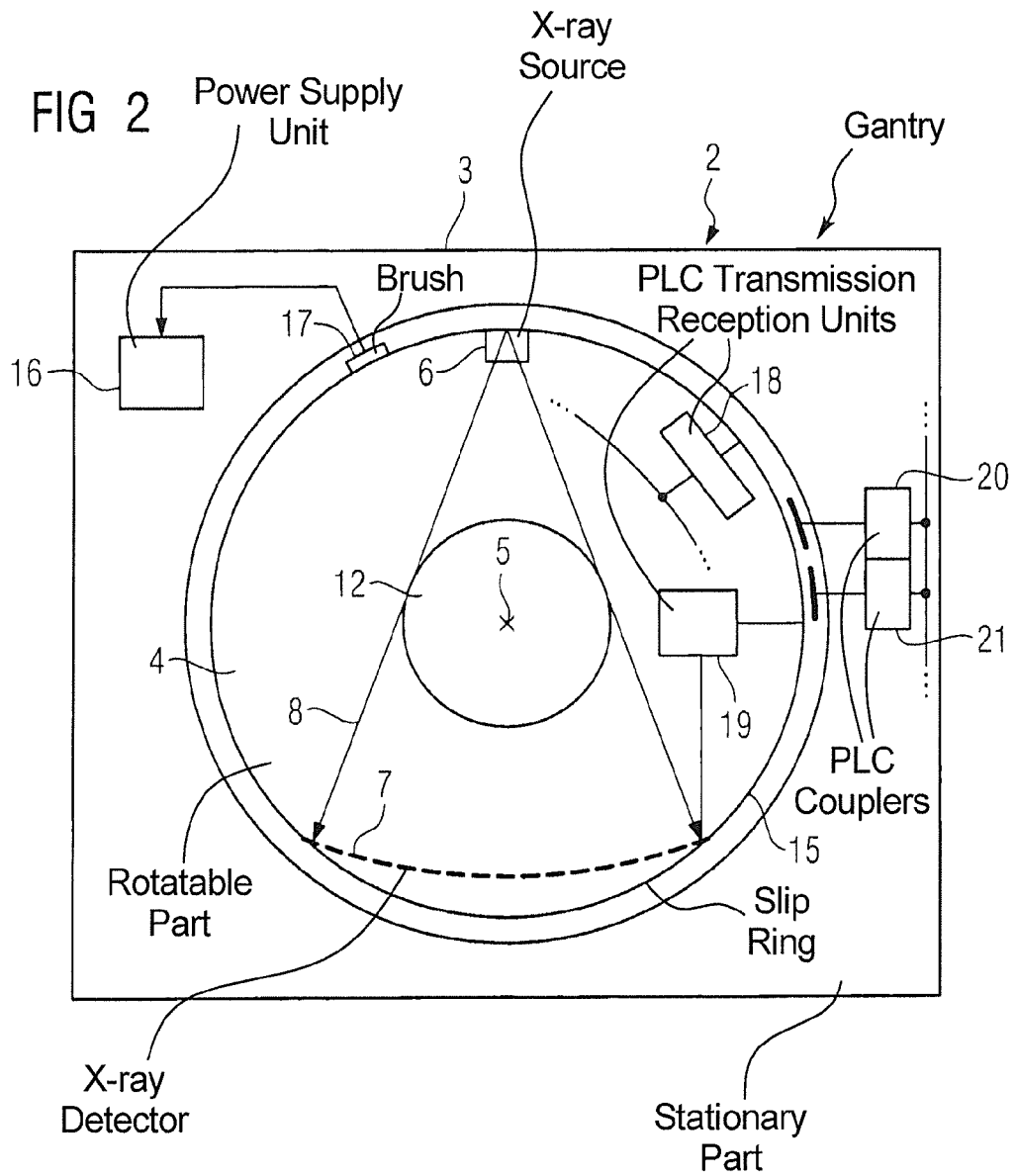

SYSTEM AND METHOD FOR TRANSFERRING DATA IN A COMPUTED TOMOGRAPHY APPARATUS

BACKGROUND OF THE INVENTION

1. Field of the Invention

The invention concerns a system and a method for data transfer between a rotatable part and a stationary part of a gantry of a computed tomography apparatus. The invention also concerns a computed tomography apparatus having such a device for data transfer.

2. Description of the Prior Art

A computed tomography apparatus, in particular an x-ray computed tomography apparatus, has a gantry with a part that can rotate relative to a stationary part. On or in the rotatable part are arranged (among other things) an x-ray source and an x-ray detector opposite one another. In the operation of the x-ray computed tomography apparatus, large quantities of measurement data accumulate during the acquisition of x-ray projections. The measurement data must be transferred from the rotating part to the stationary part of the gantry since the processing of the measurement data—in particular the reconstruction of slice images and 3D images based on the measurement data—normally ensues with an image computer located on the stationary side.

Furthermore, in the operation of the x-ray computed tomography apparatus bidirectional operating data of the x-ray computed tomography apparatus (including control data, status data etc.) must be transferred from the stationary part to the rotatable part of the gantry and from the rotatable part to the stationary part.

The data transfer between the stationary part and the rotatable part of the gantry can take place by mechanical contact (using slip rings) or without contact (for example by capacitive coupling. For example, in DE 10 2005 056 049 A1 a contact-less data transfer by capacitive coupling in a computed tomography apparatus is described. At least one stripline (strip conductor) pair for symmetrical signal transfer is attached on the rotatable part of the gantry; into which stripline pair the data to be transferred or electrical signals carrying the information are fed by a transmission module. At least one receiver element is mounted on the stationary part, this receiver element being located at a slight distance along at least one segment of the stripline pair during the relative movement of the two parts and is connected with a receiver module.

A computed tomography apparatus normally has multiple such data transmission links (routes) each formed by a stripline pair. A first data transmission link is present for the transfer of the measurement data acquired with the x-ray detector from the rotatable part of the gantry to the stationary part. A second data transmission link is provided for the transfer of operating data of the computed tomography apparatus from the stationary part to the rotatable part of the gantry, and a third data transmission link is provided for the transfer of operating data of the computed tomography apparatus form the rotatable part of the gantry to the stationary part. The second and third data transmission links serve to generate the redundancy that is necessary for the transfer of operating data in order to realize a secure data transmission between the rotatable part and stationary part of the gantry.

The provision and the parallel operation of the transmission links for data involves a not inconsiderable technical and financial cost.

Furthermore, an arrangement for transmission of electrical signals and/or energy between parts that are rotating relative to one another is known from U.S. Pat. No. 6,798,309 B2. A transmission unit has two annular electrical conductors, one transmitter and a termination element. The transmitter and the termination element are arranged diametrically opposite one another in relation to the annular electrical conductor. The two annular conductors are terminated, essentially without reflection (reflection-free termination), by the termination element. A high-resistance (high-ohmic) receiver has two conductors matched to the electrical conductors of the transmitter and that are not terminated with a reflection-free termination, and are galvanically, inductively and/or capacitively coupled with the conductors of the transmitter. The conductors of the transmitter are a symmetrically arranged conductor pair into which the transmitter symmetrically feed signals to be transmitted. The receiver can tap the signal by means of a slip contact, or inductively or capacitively.

The design of a PET scanner for small organisms is described by Lewellen, T. K. et al. in "System Integration of the MiCES small animal PET Scanner", 2004 IEEE Nuclear Science Symposium Conference Record, 16-22 Oct. 2004, Vol. 5, pp. 3316-3320. The gantry of the PET scanner has a slip ring arrangement to transfer energy and analog signals.

SUMMARY OF THE INVENTION

An object of the present invention is to provide a device, a computed tomography apparatus and a method of the aforementioned type wherein the cost for the data transfer between the stationary part and rotatable part of the gantry of the computed tomography apparatus is reduced.

According to the invention, this object is achieved by a system for a computed tomography apparatus that has a gantry with a rotatable and a stationary part, the system including at least one device for energy transfer between the rotatable part and stationary part of the gantry and at least one PLC component for data transfer between the rotatable part and stationary part of the gantry via the at least one device for energy transfer, wherein the transfer of energy and the transfer of data advantageously ensue simultaneously or in parallel or in alternation via the device for energy transfer.

According to the invention a separate physical device and a separate physical path for transfer of data between the rotatable part and stationary part of the gantry of a computed tomography apparatus are omitted, and instead the data are transferred by a PLC (Power Line Communication) via the device for energy transfer that is present anyway.

In this way two physical transmission links for data can be spared, which not only reduces the technical cost but also the financial cost for the data transfer between a rotating part and a stationary part of a gantry of a computed tomography apparatus.

In an embodiment of the invention, the at least one device for energy transfer has at least one annular transfer element. The at least one annular transfer element is advantageously at least one slip ring for energy transfer, as is known in computed tomography apparatuses.

In a further embodiment of the invention, the data transfer between the rotatable part and stationary part of the gantry ensues bidirectionally via the at least one device for energy transfer.

According to a further embodiment of the invention, the data transfer ensues with or without contact via at least one PLC component. If at least one slip ring is located on the rotatable part of the gantry and at least one PLC component is located on the stationary part of the gantry, for data transfer between the rotatable part of the gantry and the stationary part the at least one PLC component can be connected via brushes with the at least one slip ring for data transfer with contact. Alternatively, for data transfer the at least one PLC component can couple and/or decouple PLC signals without contact (inductively, for example) in the at least one slip ring. In this case the at least one PLC component according to a variant of the invention is a PLC coupler for contact-less coupling and/or decoupling of PLC signals.

According to a further variant of the invention, the data transfer takes place in a frequency range from 1 MHz to 40 MHz.

The aforementioned object also is achieved in accordance with the invention by a computed tomography apparatus that has at least one system as described above for data transfer between a rotatable part and stationary part of a gantry of the computed tomography apparatus.

In an embodiment of the invention at least one slip ring is arranged at the rotatable part of the gantry and is connected with at least one PLC component arranged at the rotatable part of the gantry to receive and/or to send PLC signals for the data transfer.

According to a further embodiment of the invention, the stationary part of the gantry has at least one PLC coupler for contact-less coupling and/or decoupling of PLC signals into or, respectively, from the at least one slip ring.

The aforementioned object also is achieved in accordance with the invention by a method for a computed tomography apparatus that has a gantry with a rotatable part and a stationary part in which data are transferred between the rotatable part and the stationary part of the gantry, advantageously simultaneously or in parallel with or in alternation with the energy via a system for energy transfer, wherein the data transfer takes place via at least one device for energy transfer between the rotatable part and stationary part of the gantry with at least one PLC component.

According to an embodiment of the inventive method, operating data of the computed tomography apparatus and measurement data generated by the computed tomography apparatus are thereby transferred.

BRIEF DESCRIPTION OF THE DRAWINGS

FIG. 1 shows an x-ray computed tomography apparatus in accordance with the invention.

FIG. 2 is a cross-section of the gantry of the x-ray computed tomography apparatus of FIG. 1

DESCRIPTION OF THE PREFERRED EMBODIMENTS

Identical or functionally identical elements are provided with the same reference characters throughout the figures. The representations in the figures are schematic and not necessarily true to scale. The x-ray computed tomography apparatus 1 shown in FIG. 1 and FIG. 2 is discussed in the following and without limitation of the generality only insofar as is deemed necessary to understand the invention.

The x-ray computed tomography apparatus 1 shown in FIG. 1 has a gantry 2 with a stationary part 3 and with a part 4 that is rotatable around a system axis 5. In the exemplary embodiments of the invention, the rotatable part 4 has an x-ray system which comprises an x-ray source 6 and an x-ray detector 7 that are arranged opposite one another on the rotatable part 4. In the operation of the x-ray computed tomography apparatus 1, x-ray radiation 8 emanates from the x-ray source 6 in the direction of the x-ray detector 7, penetrates a measurement subject and is detected by the x-ray detector 7 in the form of measurement data or, respectively, measurement signals.

The x-ray computed tomography apparatus 1 furthermore has a patient bed 9 to support a patient P to be examined. The patient bed 9 has a bed base 10 on which is arranged a patient bearing plate 11 that is provided to actually support the patient P. The patient bearing plate 11 can be displaced relative to the bed base 10 in the direction of the system axis 5 such that it, together with the patient P, can be introduced into the opening 12 of the gantry 2 (which presently defines a cylindrical measurement field) to acquire 2D x-ray projections of the patient P, for example in a spiral scan. The computational processing of the 2D x-ray projections acquired with the x-ray system, namely the reconstruction of slice images, 3D images or a 3D data set based on the measurement data or the measurement signals of the 2D x-ray projections, ensues with an image computer 13 of the x-ray computed tomography apparatus 1. Such slice images or 3D images can be presented at a display device 14.

To operate the components of the x-ray computed tomography 1 that are arranged on the rotatable part 4, for example the x-ray source 6 and the x-ray receiver 7, these must be supplied with electrical power. To supply power to the components, in the exemplary embodiment of the invention the x-ray computed tomography apparatus 1 has a device for energy transfer that includes annular transfer elements in the form of annular, closed slip rings.

Such a slip ring 15 is schematically shown in FIG. 2. The slip ring 15 is fed by a power supply unit 16 arranged at the stationary part 3: in the exemplary embodiment of the invention the slip ring 15 is contacted with a brush 17. At the rotatable part 4 the slip ring is connected (the manner is not shown) with electrical components that are to be supplied, for example the x-ray source 6 and/or the x-ray detector 7.

Furthermore, in the operation of the x-ray computed tomography apparatus 1 operating data about operating states of components, control data and regulatory data are to be transferred both from the stationary part 3 to the rotatable part 4 and from the rotatable part 4 to the stationary part 3 of the gantry 2. Moreover, large quantities of measurement data acquired with the x-ray detector 7 are to be transferred from the rotatable part 4 to the stationary part 3.

According to the invention, the transfer of such data likewise ensues by means of PLC (Power Line Communication) via the slip rings provided for power supply, and in fact advantageously ensues simultaneously or in parallel with the energy transfer.

In the exemplary embodiment of the invention, a PLC transmission and reception unit 18 is present on the rotatable part 4 to send and receive operating data in the form of PLC signals, which PLC transmission and reception unit 18 is connected with the slip ring 15 and with the components arranged on the rotatable part 4. The PLC transmission and reception unit 18 can receive operating data fed into the slip ring 15 as PLC signals, or can itself feed operating data as PLC signals into the slip ring 15.

Furthermore, a second PLC transmission and reception unit 19 is arranged on the rotatable part 4 to transmit the measurement data or measurement signals generated with the x-ray detector 7, which PLC transmission and reception unit 19 is connected with the x-ray detector 7 and the slip ring 15. The PLC transmission and reception unit 19 can feed measurement signals in the form of PLC signals into the slip ring 15.

A first PLC coupler 20 to send and receive operating data in the form of PLC signals and a second PLC coupler 21 to receive the measurement signals in the form of PLC signals are arranged at the stationary part 3. In the case of the present exemplary embodiments of the invention, the two PLC couplers 20 and 21 couple and decouple PLC signals in the slip ring without contact (inductively).

In this way operating data can be transferred bidirectionally and measurement data or, respectively, measurement signals can be transferred unidirectionally (optionally bidirectionally as well) between the stationary part 3 and the rotatable part 4 of the gantry 2 by means of PLC via a slip ring (for instance the slip ring 15) provided for power supply, which transfer takes place simultaneously or in parallel with the energy transfer, whereby separate transmission links provided exclusively for data transfer can be omitted.

Alternatively, the PLC couplers 20 and 21 can also be replaced with PLC transmission and/or reception units that are connected with the slip ring 15 via brushes (not shown) so that in this case the data transfer takes place with contact.

In the exemplary embodiment of the invention the data transfer by means of PLC sis ensues in a frequency range from 1 MHz to 40 MHz.

As mentioned, the x-ray computed tomography apparatus 1 can have multiple slip rings provided for power supply, wherein data can be transferred via any of these slip rings by means of the PLC.

In contrast to the described exemplary embodiment of the invention, the slip rings can also be arranged on the stationary part of the gantry so that PLC couplers are present on the rotatable part 4 of the gantry, or PLC transmission and/or reception units can contact the slip ring (for example by means of brushes).

The specification of the frequency range for the transfer of data by means of PLC signals is to be understood merely as an example and can deviate from this example.

Although modifications and changes may be suggested by those skilled in the art, it is the intention of the inventor to embody within the patent warranted hereon all changes and modifications as reasonably and properly come within the scope of his contribution to the art.

I claim as my invention:

1. A system for transferring data in a computed tomography apparatus, said computed tomography apparatus comprising a gantry having a stationary part and a rotatable part that is rotatable relative to said stationary part, said system comprising:
    at least one energy transfer device that transfers energy between said rotatable part and said stationary part of said gantry; and
    at least one power line communication (PLC) component that transfers data between said rotatable part and said stationary part of said gantry via said at least one energy transfer device.

2. A system as claimed in claim 1 wherein said at least one energy transfer device comprises at least one annular transfer element.

3. A system as claimed in claim 1 wherein said at least one energy transfer device comprises at least one slip ring.

4. A system as claimed in claim 1 wherein said at least one PLC component bidirectionally transfers said data between said rotatable part and said stationary part of said gantry via said at least one energy transfer device.

5. A system as claimed in claim 1 wherein said PLC component transfers said data between said rotatable part and said stationary part via a data transfer path comprising a mechanical contact.

6. A system as claimed in claim 1 wherein said PLC component transfers said data between said rotatable part and said stationary part via a data transfer path having no mechanical contacts.

7. A system as claimed in claim 1 wherein said at least one PLC component is a PLC coupler that couples and decouples PLC signals without mechanical contact.

8. A system as claimed in claim 1 wherein said PLC component transfers said data in a frequency range between 1 and 40 MHz.

9. A computed tomography apparatus comprising:
    a gantry comprising a stationary part and a rotatable part that is rotatable relative to said stationary part;
    at least one energy transfer device that transfers energy between said rotatable part and said stationary part of said gantry; and
    at least one power line communication (PLC) component that transfers data between said rotatable part and said stationary part of said gantry via said at least one energy transfer device.

10. A computed tomography apparatus as claimed in claim 9 comprising at least one slip ring located at said rotatable part of said gantry, in mechanical connection with said at least one PLC component to receive and send PLC signals.

11. A computed tomography apparatus as claimed in claim 10 wherein said PLC component comprises a PLC coupler located at said stationary part of said gantry that couples and decouples PLC signals into and out of said slip ring.

12. A method for transferring data between a stationary part, and a rotatable part that is rotatable relative to stationary part, of a gantry of a computed tomography apparatus, comprising the steps of:
    transferring energy between said rotatable part and said stationary part of the gantry via an energy transfer device; and
    transferring data between said rotatable part and said stationary part of said gantry via at least one power line communication (PLC) component via said at least one energy transfer device.

13. A method as claimed in claim 12 comprising transferring operating data of said computed tomography apparatus and measurement data generated by said computed tomography apparatus as said data that are transferred via said at least one PLC component via said at least one energy transfer device.

* * * * *